(12) United States Patent
Ogawa et al.

(10) Patent No.: US 10,369,290 B2
(45) Date of Patent: Aug. 6, 2019

(54) SYRINGE

(71) Applicant: Taisei Kako Co., Ltd., Osaka (JP)

(72) Inventors: Yukihiro Ogawa, Osaka (JP); Yuji Tanaka, Kanagawa (JP)

(73) Assignee: Taisei Kako Co., Ltd., Osaka (JP)

( * ) Notice: Subject to any disclaimer, the term of this patent is extended or adjusted under 35 U.S.C. 154(b) by 95 days.

(21) Appl. No.: 15/564,143

(22) PCT Filed: Feb. 15, 2016

(86) PCT No.: PCT/JP2016/054239
§ 371 (c)(1),
(2) Date: Oct. 3, 2017

(87) PCT Pub. No.: WO2016/170825
PCT Pub. Date: Oct. 27, 2016

(65) Prior Publication Data
US 2018/0078708 A1    Mar. 22, 2018

(30) Foreign Application Priority Data
Apr. 20, 2015   (JP) .................. 2015-085846

(51) Int. Cl.
*A61M 5/315*     (2006.01)
*A61M 5/31*      (2006.01)
(Continued)

(52) U.S. Cl.
CPC ........ *A61M 5/31511* (2013.01); *A61M 5/281* (2013.01); *A61M 5/3129* (2013.01);
(Continued)

(58) Field of Classification Search
CPC .............. A61M 5/31511; A61M 5/281; A61M 5/3129; A61M 5/3257; A61M 5/3275;
(Continued)

(56) References Cited

U.S. PATENT DOCUMENTS 8,251,951 B2 * 8/2012 Suzuki ................. A61M 5/326
604/110
2010/0042047 A1   2/2010 Suzuki
(Continued)

FOREIGN PATENT DOCUMENTS

JP    2013500745 A    1/2013
JP    2013544165 A   12/2013
(Continued)

OTHER PUBLICATIONS

International Search Report dated May 10, 2016.

*Primary Examiner* — Nathan R Price
*Assistant Examiner* — Melissa A Snyder
(74) *Attorney, Agent, or Firm* — Wood, Phillips, Katz, Clark & Mortimer

(57) ABSTRACT

The present invention provides a next-generation pre-filled syringe having a reduced number of components and requiring reduced costs and including a safety mechanism for preventing needlestick injuries. In the syringe of the present invention, elastic engagement members 11 of the cover 6 engage the injection needle 5 so as to prevent the injection needle 5 from being withdrawn from the elastic engagement members 11 of the cover in a retracted state toward the base end, and the elastic engagement members and injection needle are disengaged from each other as the elastic engagement members 11 are diametrically expanded/deformed. Further, the plunger 4 includes an integrated deformation-prevention part 41 covering the outer peripheries of the plurality of elastic engagement members 11 so as to prevent the elastic engagement members 11 and the injection needle 5 from being disengaged from each other as the elastic engagement members 11 are diametrically expanded/deformed.

5 Claims, 18 Drawing Sheets

(51) Int. Cl.
  *A61M 5/32* (2006.01)
  *A61M 5/28* (2006.01)
  *A61M 5/34* (2006.01)
(52) U.S. Cl.
  CPC ........ *A61M 5/3257* (2013.01); *A61M 5/3275* (2013.01); *A61M 5/3202* (2013.01); *A61M 5/3286* (2013.01); *A61M 5/34* (2013.01); *A61M 2005/3131* (2013.01); *A61M 2005/3247* (2013.01); *A61M 2205/0216* (2013.01); *A61M 2205/584* (2013.01)
(58) Field of Classification Search
  CPC .. A61M 2005/3131; A61M 2005/3261; A61M 5/3243; A61M 2005/3254; A61M 2005/3268
  See application file for complete search history.

(56) References Cited

U.S. PATENT DOCUMENTS

| | | |
|---|---|---|
| 2012/0150125 A1 | 6/2012 | Karlsson et al. |
| 2013/0245563 A1 | 9/2013 | Mercer et al. |
| 2016/0067421 A1 | 3/2016 | Ogawa et al. |

FOREIGN PATENT DOCUMENTS

| | | |
|---|---|---|
| WO | 2008072715 A1 | 6/2008 |
| WO | 2014175237 A1 | 10/2014 |

\* cited by examiner

SYRINGE

TECHNICAL FIELD

The present invention relates a syringe.

BACKGROUND ART

The present inventors have long been developing disposable syringes whose needle can remain retracted in the body until injection and can be retracted back into the body after injection in order to prevent the patient from accidentally hurting himself/herself with the needle when injecting biomedical anticancer drugs or antirheumatic drugs at home, examples of which are disclosed in Patent Documents 1 and 2 provided below.

PRIOR ART

Patent Documents

Patent Document 1: JP 2013-519 A
Patent Document 2: JP 2014-212832 A

In each of these conventional syringes, the injection needle is placed within the cover (i.e. first holder member) and a plunger (i.e. second holder member) during storage before use. During storage, the cover and plunger are placed against each other to prevent the plunger from being thrusted into the cover. During use, the cover and plunger are rotated relative to each other to reduce the total axial length of the cover and plunger such that the tip of the injection needle protrudes outward from the distal-end portion of the cover and, then, the syringe barrel (or vial) is thrusted into the cover and plunger to achieve administration of the liquid drug. Further, after the completion of administration, the cover and plunger are extended along the axial direction to place the injection needle back in these members and, then, the cover and plunger are rotated relative to each other to lock them in order to prevent the injection needle from protruding again, thereby enabling safe disposal.

To provide the above-discussed functions, in each of the conventional syringes described above, each of the cover and plunger includes a plurality of elastic engagement members (i.e. columnar member) that fit to the corresponding elastic engagement members and all the elastic engagement members engage steps provided on the outer periphery of the needle base of the injection needle, and a key cylinder (i.e. jacketing sleeve) covers the outer periphery of the elastic engagement members to prevent the elastic engagement members from being disengaged from the steps.

SUMMARY OF THE INVENTION

Problems to be Solved by the Invention

These conventional syringes have a large number of components and are thus high-cost.

In view of this, an object of the present invention is to provide a syringe having a reduced number of components and having substantially the same functions as the above-described conventional syringes.

Means for Solving the Problems

To solve the above-stated problems, the present invention features the following technical means.

The syringe of the present invention includes: a syringe barrel having an open distal-end portion and having an interior space to be filled with a liquid drug; a gasket fitted into the syringe barrel to seal in the liquid drug; an injection needle having a base-end portion adapted to pierce through the gasket at least during administration of the liquid drug; a plunger attached to the gasket and holding the injection needle; and a cover provided adjacent to a distal-end portion of the plunger.

The cover includes a plurality of first elastic engagement members for holding the injection needle, the first elastic engagement members being spaced apart from each other in the circumferential direction and capable of being deformed so as to be diametrically expanded. The cover is capable of moving in an axial direction relative to the injection needle between a state where a distal-end portion of the injection needle is housed within the cover and a state where the distal-end portion of the injection needle protrudes from a distal-end portion of the cover. Further, the elastic engagement members of the cover in the housing state and the injection needle engage so as to prevent the injection needle from being withdrawn from the elastic engagement members of the cover. This engagement is released as the elastic engagement members are diametrically expansively deformed. Preferably, the elastic engagement members may be constituted by columnar members as disclosed in Patent Documents 1 and 2 listed above; alternatively, they may have any other shape than columnar.

The cover may be composed of two members, i.e. a cylindrical first cover member covering the outer periphery of the injection needle and a second cover member mounted on the distal-end portion of the sleeve. At the axis center of the second cover member may be provided a needle retraction hole through which the tip of the injection needle may be projected and retracted.

The present invention is characterized in that the plunger includes an integrated deformation-prevention part covering the outer peripheries of the plurality of elastic engagement members so as to prevent the engagement from being released. Such disengagement would occur by the elastic engagement members being diametrically expansively deformed. Meanwhile, the deformation-prevention part may permit some diametric expansion/deformation of the elastic engagement members.

In this inventive syringe, the deformation-prevention part of the plunger prevents the elastic engagement members from being deformed to prevent the elastic engagement members and injection needle from being disengaged, which means that such disengagement can be prevented without providing a key cylinder separate from the plunger, thereby providing a structure that is unlikely to be disintegrated while reducing the number of components.

Starting from the above-described inventive syringe, the plunger may include a plurality of second elastic engagement members for holding the injection needle, the plurality of second elastic engagement members being separated from each other in the circumferential direction and capable of being diametrically expanded/deformed, and the deformation-prevention part may be located closer to the distal end than the second elastic engagement members.

Further, the cover may be rotatable relative to the plunger between a locked position where the plurality of second elastic engagement members of the plunger are aligned with the plurality of first elastic engagement members to be arranged in the axial direction and an unlocked position where the plurality of second elastic engagement members face a plurality of spaces defined by the first elastic engagement members. Preferably, by thrusting the plunger into the cover in the unlocked position toward the distal end, the plurality of first elastic engagement members alternatively fit to the plurality of second elastic engagement members to reduce the total length of the cover and plunger. Further, the deformation-prevention part may cover the outer peripheries of the plurality of first elastic engagement members in both the locked position and the unlocked position, thereby providing a structure that is unlikely to be disintegrated before and after the above-described rotation operation, while reducing the number of components.

Furthermore, the cover may include: a cylindrical portion, the syringe barrel being inserted into the cylindrical portion to be movable in the axial direction; a cover plate closing a distal-end opening of the cylindrical portion; the plurality of first elastic engagement members extending from the cover plate toward the base end as determined along the axial direction; and a plurality of holding members located between the plurality of first elastic engagement members and extending from the cover plate toward the base end as determined along the axial direction. The cover plate may be integral with the second cover member, and the cylindrical portion may be constituted by the first cover member. Preferably, the holding members and the first elastic engagement members are separated from each other in the circumferential direction, and the first elastic engagement members may be elastically deformable such that their base-end ends move radially outward. Further, the first elastic engagement members may extend farther toward the base end than the holding members, thereby providing the spaces adjacent to the base-end ends of the holding members. The plurality of holding members work together with the plurality of first elastic engagement members to hold the injection needle such that the injection needle can be held by the cover more stably.

The axial length of the first elastic engagement members may be larger than that of the second elastic engagement members, thereby providing sufficient thrust stroke length of the plunger relative to the cover while providing the above-described deformation-prevention part. If the first elastic engagement members have a large length, they can easily be diametrically expanded/deformed; however, according to the present invention, the deformation-prevention part prevents diametric expansion/deformation to prevent the injection needle from slipping out of the first elastic engagement members toward the base end. Meanwhile, the second elastic engagement members have a relatively small length to prevent elastic deformation, thereby preventing the injection needle from being disengaged from the second elastic engagement members without providing a member for preventing the second elastic engagement members from being diametrically expanded/deformed.

The deformation-prevention part is preferably cylindrical in shape, and its inner diameter may be substantially equal to the outer diameter of the plurality of second elastic engagement members. The second elastic engagement members may have an outer diameter with an arc-shaped cross section; alternatively, they may have any geometry such as a rectangular cross section, in which case "outer diameter of the second elastic engagement members" means the outer diameter of the portions with the maximum radius as measured from the rotational axis center.

The outer periphery of the deformation-prevention part of the plunger may be covered with the cover, and a pair of recesses may be provided in a pair of opposite portions of the deformation-prevention part of the plunger arranged in a diametrical direction and occupying a part of the deformation-prevention part as determined along the axial direction, each recess extending through in a direction perpendicular to the diametrical direction. A peephole may be provided in the cover. The peephole faces one of the recesses such that they are arranged in the direction of through-extension when the cover is at one of the locked position and the unlocked position, and faces the deformation-prevention part when the cover is at the other position such that the peephole is closed by the deformation-prevention part. This arrangement will allow the user to determine, by visual inspection, whether the cover has been rotated relative to the plunger depending on whether the peephole is closed by the deformation-prevention part, thereby improving the convenience for the user during operation.

Effects of the Invention

The syringe of the present invention provides a new syringe configuration that provides substantially the same functions as the conventional syringes discussed above, while reducing the number of components, thereby significantly reducing manufacture costs, and the smaller number of components also makes it possible to reduce the size of the syringe.

EMBODIMENTS FOR CARRYING OUT THE INVENTION

Figure 1:
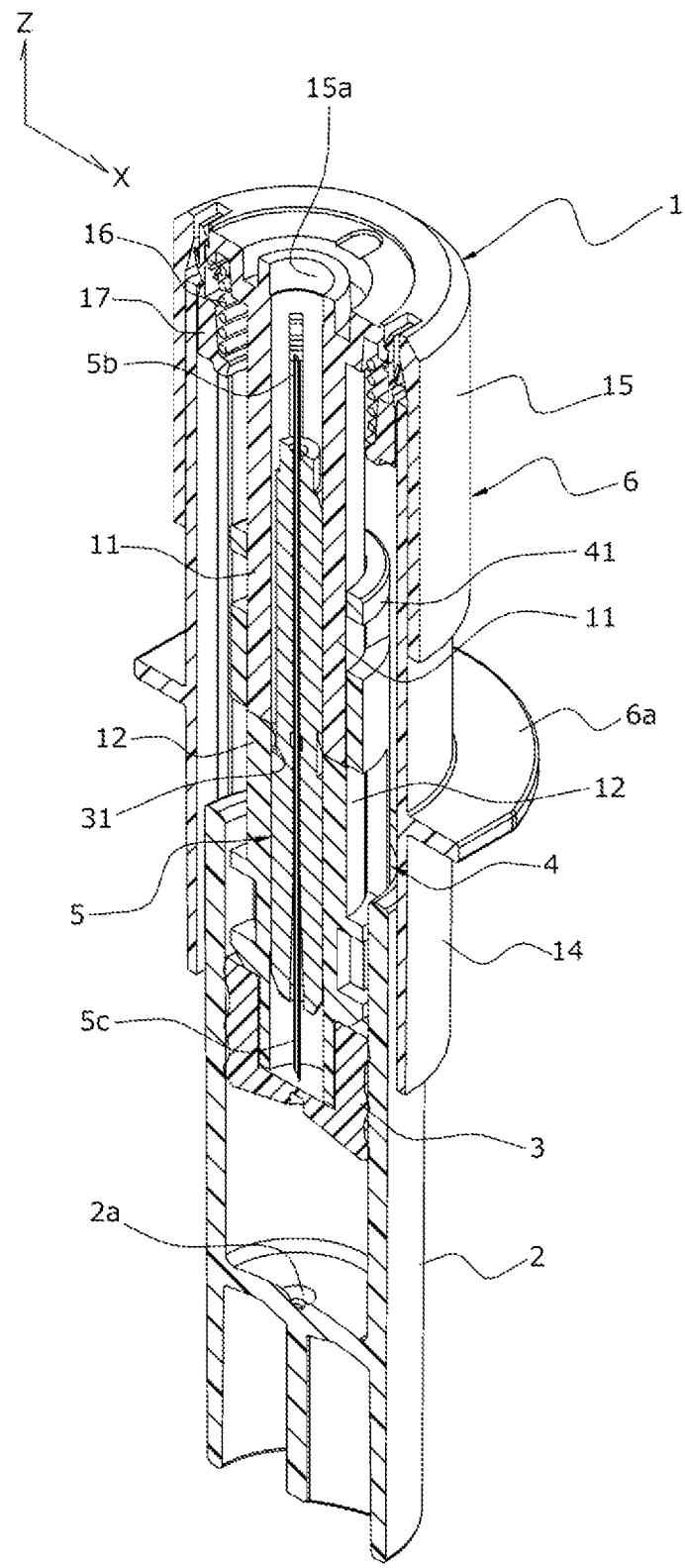
FIG. 1 is a perspective vertical cross section (X-Z cross section) of a syringe according to an embodiment of the present invention during storage.

Preferred embodiments of the present invention will now be described with reference to the drawings.

FIGS. 1 to 16 show a syringe 1 according to an embodiment of the present invention and its components. As used herein, "distal end" means the distal end of the injection needle, and "base end" means the base end of the injection needle. That is, in the drawings, the upward direction is the direction toward the distal end, and the downward direction is the direction toward the base end.

The syringe 1 of the present embodiment includes a syringe barrel 2 having the shape of a bottomed cylinder and made of transparent or translucent glass or synthetic resin, a gasket 3 sealingly introduced into the syringe barrel 2 through the distal-end opening so as to be movable in the axial direction, a plunger 4 for thrusting the gasket 3 into the syringe barrel 2 toward the base end, a double-ended injection needle 5 attached to the plunger 4 so as to be movable in the axial direction, and a cover 6 covering the outer periphery of the injection needle 5, these components being positioned to be concentric.

The cover 6 includes a cylindrical first cover member 14 provided with an integral finger-hook flange 6a located on the outer periphery of an intermediate portion thereof as determined along the axial direction, and a second cover member 15 mounted on the distal-end portion of the first cover member 14. The syringe barrel 2 is inserted into the first cover member 14 through its base-end portion. The second cover member 15 engages with the first cover member 14 so as to be not rotatable and be movable in the axial direction relative to the first cover member by a small amount, where, during storage and during administration of the liquid drug, the second cover member 15 is engagingly held by the first cover member 14 at a compressed position in which the total axial length of the second cover member 15 and first cover member 14 is reduced, and, after administration, the covers can be moved to an extended position in which the second cover member 15 is extended in the axial direction.

Figure 2:
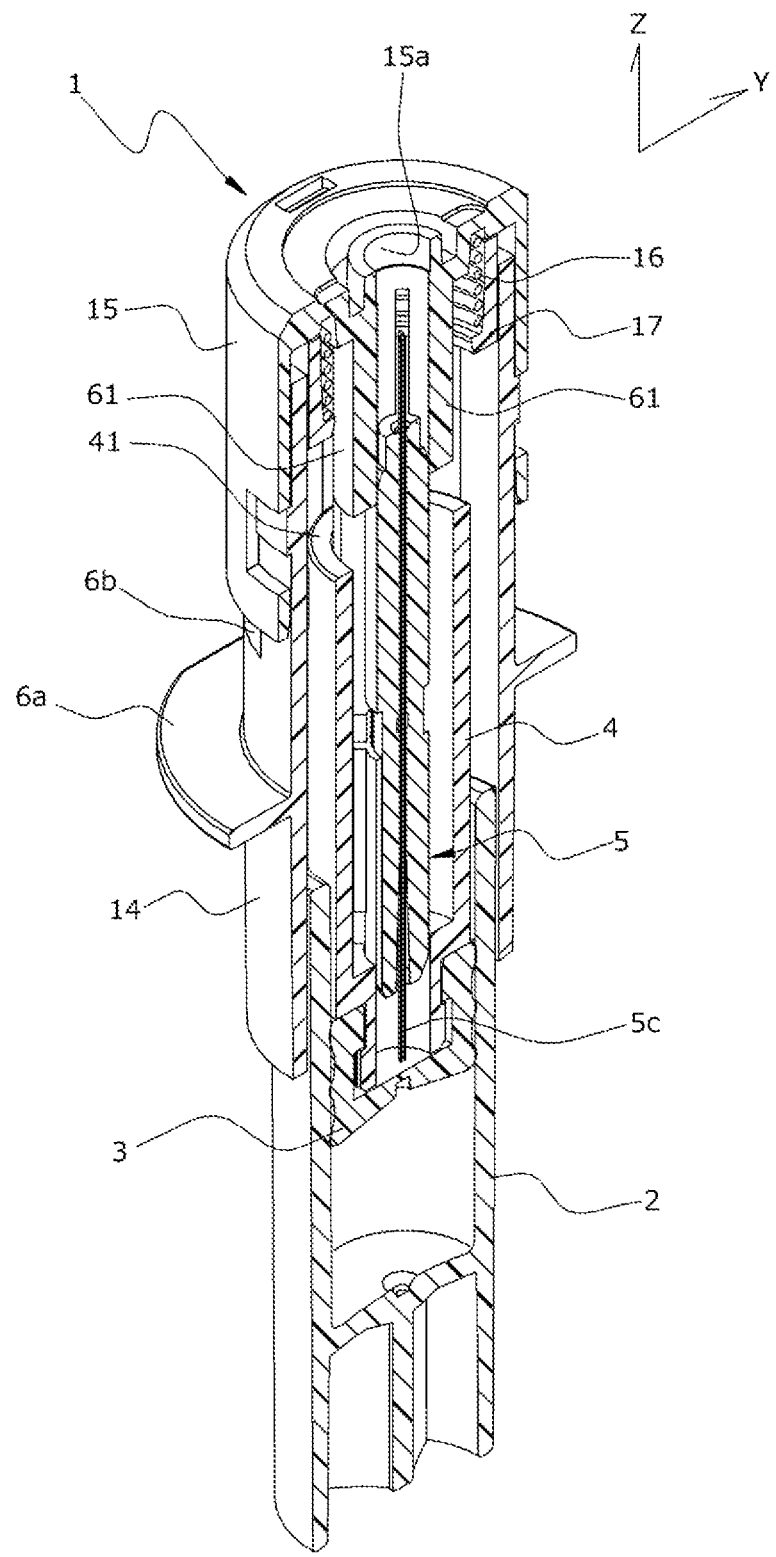
FIG. 2 is another perspective vertical cross section (Y-Z cross section) of the syringe in the state shown in FIG. 1.

The second cover member 15 includes a cylindrical portion fitted around the first cover member 14 and a cover plate (i.e. top plate) covering the distal-end opening of the cylindrical portion, these members being integral with each other, and, as shown in FIGS. 1 and 2, at the axis center of the this cover plate is provided a needle retraction hole 15a through which the distal-end needle portion 5b of the injection needle 5 may be projected and retracted.

Figure 10:
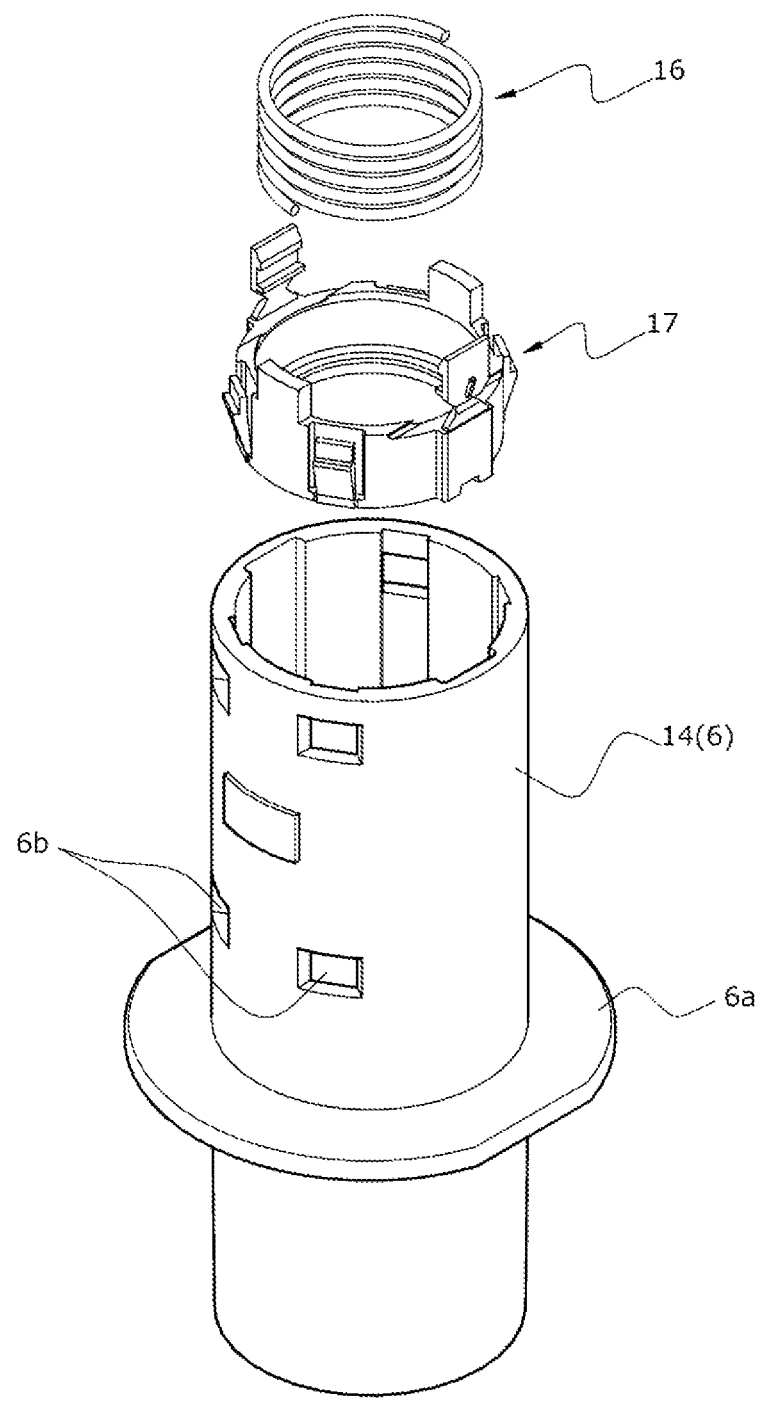
FIG. 10 is a perspective exploded view of the spring, spring holder and second cover member.

Inside the second cover member 15 are provided a coil spring 16 and a spring holder 17 for holding the spring 16 whiling keeping the spring compressed in the axial direction. This spring holder 17 and the associated automatic retraction functionality for the injection needle after use are the same as disclosed in Patent Document 1, as shown in FIG. 10; Patent Document 1 is hereby incorporated by reference and these features will not be described in detail.

The syringe barrel 2 is filled with a predetermined amount of a liquid drug in an aseptic room, and the gasket 3 is sealingly introduced into the syringe barrel 2 so as to seal in the liquid drug. A small indentation 2a is provided at the center of the bottom wall of the syringe barrel 2. While an end cap is attached to the base-end portion of the syringe barrel of the syringe disclosed in Patent Document 1, an end cap is omitted in the syringe of the present embodiment in order to reduce the number of components, where the base-end portion itself of the syringe barrel extends toward the axis. Further, while a stopper is attached to the distal-end opening of the syringe barrel of the syringe disclosed in Patent Document 1, this stopper is omitted according to the present embodiment.

Figure 4:
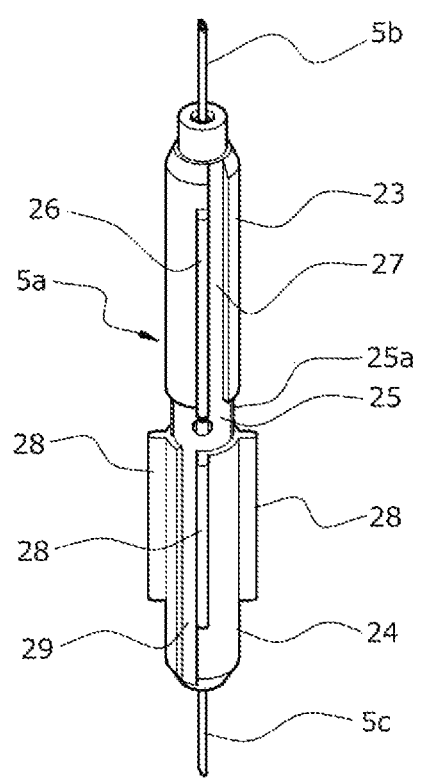
FIG. 4 is a perspective view of the injection needle.
Figure 5:
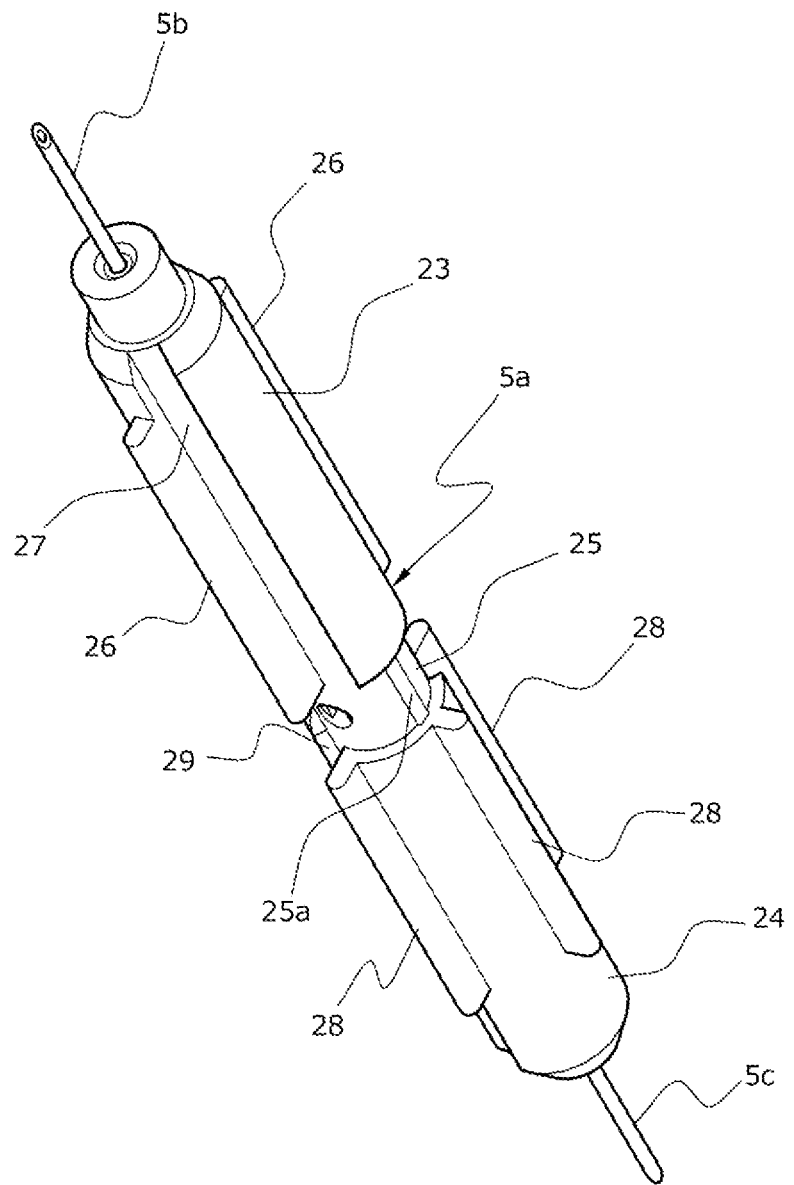
FIG. 5 is a perspective view of the injection needle as viewed in another direction.

As shown in FIGS. 4 and 5, the injection needle 5 includes a columnar needle base 5a and a needle tube extending through the needle base 5a in the axial direction. The needle tube protrudes from both ends of the needle base 5a as determined along the axial direction, where the portion protruding toward the distal end constitutes the distal-end needle portion 5b, while the portion protruding toward the base end constitutes the base-end needle portion 5c. A sharply cut edge is provided on the tip of each of the needle portions 5b and 5c.

The gasket 3 is hermetically fitted around the base-end portion of the plunger 4. Further, the axis-center portion of the gasket 3 has a smaller wall thickness so as to be easily pierced through by the base-end needle portion 5c of the injection needle 5. As shown in FIGS. 1 and 2, during storage before administration, the base-end needle portion 5c of the injection needle 5 is separated from the gasket 3 toward the distal end in the axial direction.

Figure 6:
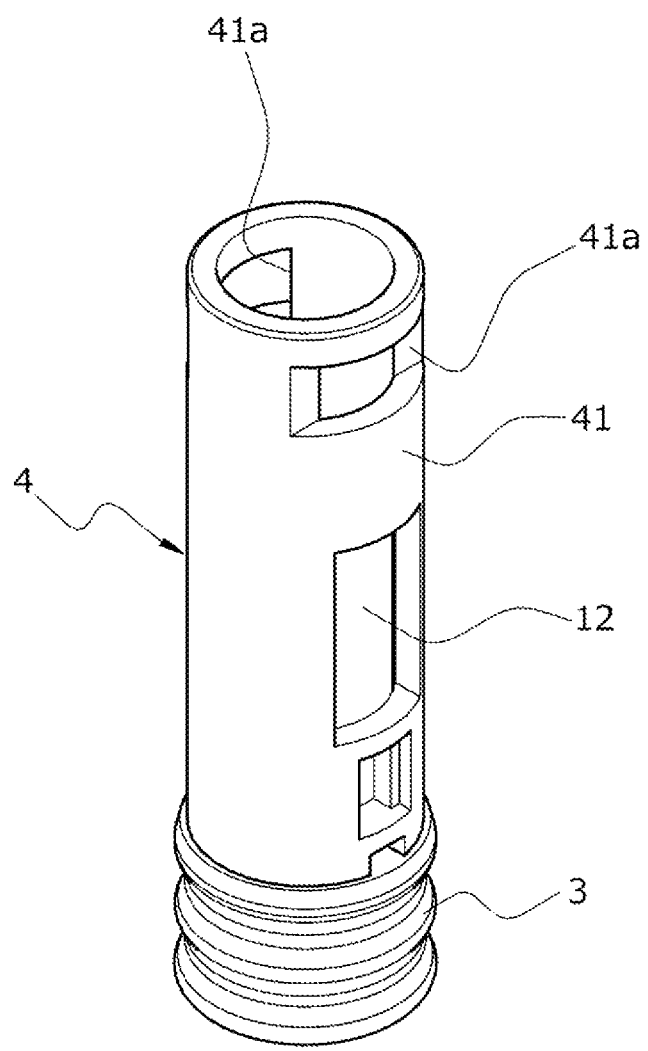
FIG. 6 is a perspective view of the plunger and gasket.
Figure 7:
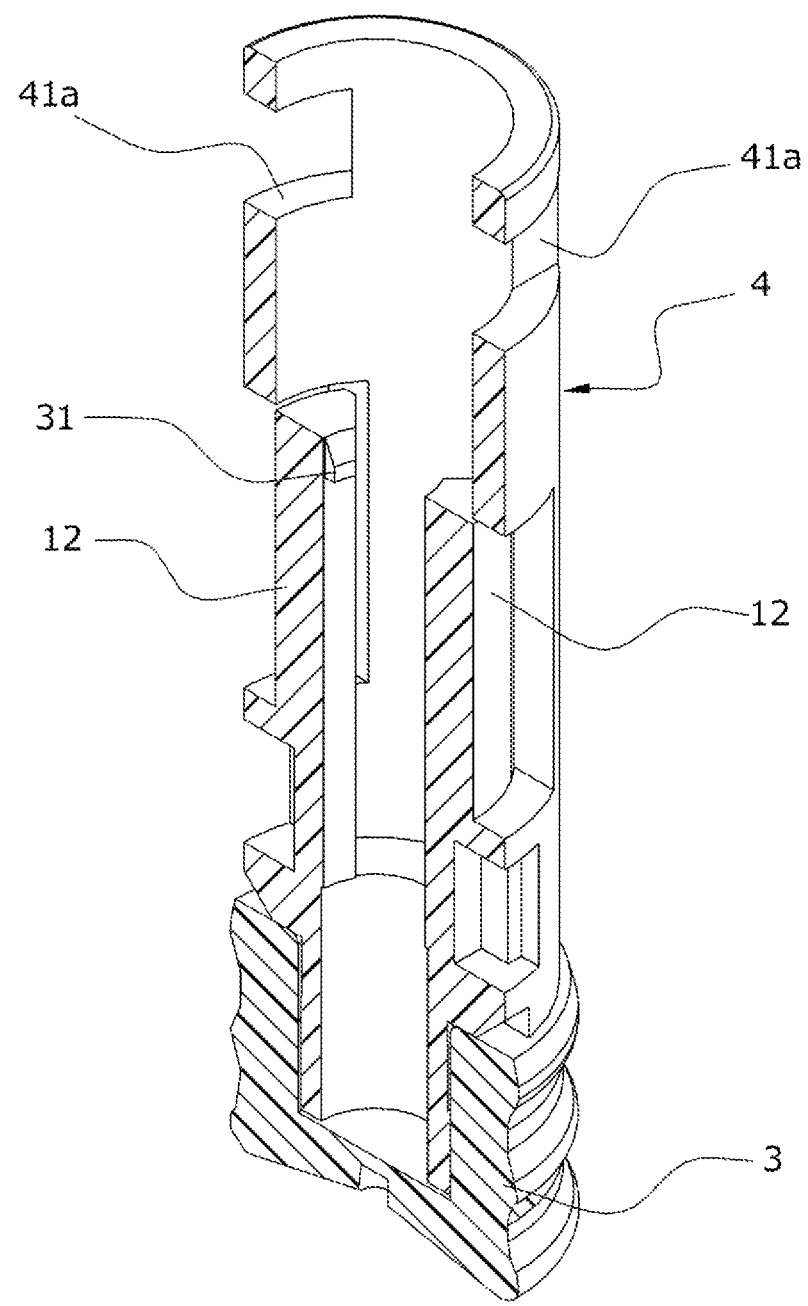
FIG. 7 is a perspective vertical cross section of the plunger and gasket.
Figure 8:
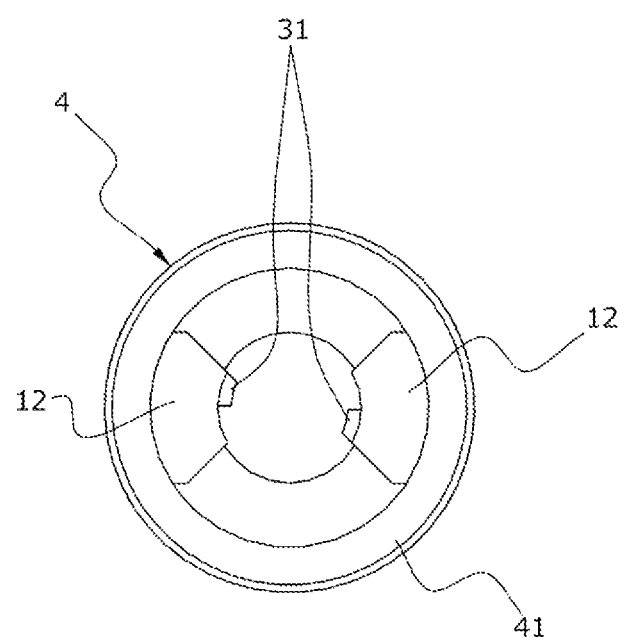
FIG. 8 is a top view of the plunger.

The plunger 4 has the shape of a hollow cylinder with a bore extending therethrough in the axial direction, as shown in FIGS. 6 to 8, and the injection needle 5 is held in this plunger 4.

The plunger 4, injection needle 5, and cover 6 constitute a safe operation mechanism for preventing an inadvertent or careless operation to prevent an accident by the injection needle 5. This safe operation mechanism includes a pair of first elastic engagement members 11 integral with the cover 6 and fittable around the needle base 5a in the direction from the distal end for holding the injection needle 5, and a pair of second elastic engagement members 12 integral with the plunger 4 and fittable around the needle base 5a in the direction from the base end for holding the injection needle 5. Each of the elastic engagement members 11 and 12 has the shape of a column with an arc-shaped transverse cross section. The pair of first elastic engagement members 11 are separated in the circumferential direction and, particularly, opposite in a diametrical direction according to the present embodiment. Similarly, the pair of second elastic engagement members 12 are separated in the circumferential direction and opposite in a diametrical direction.

Figure 11:
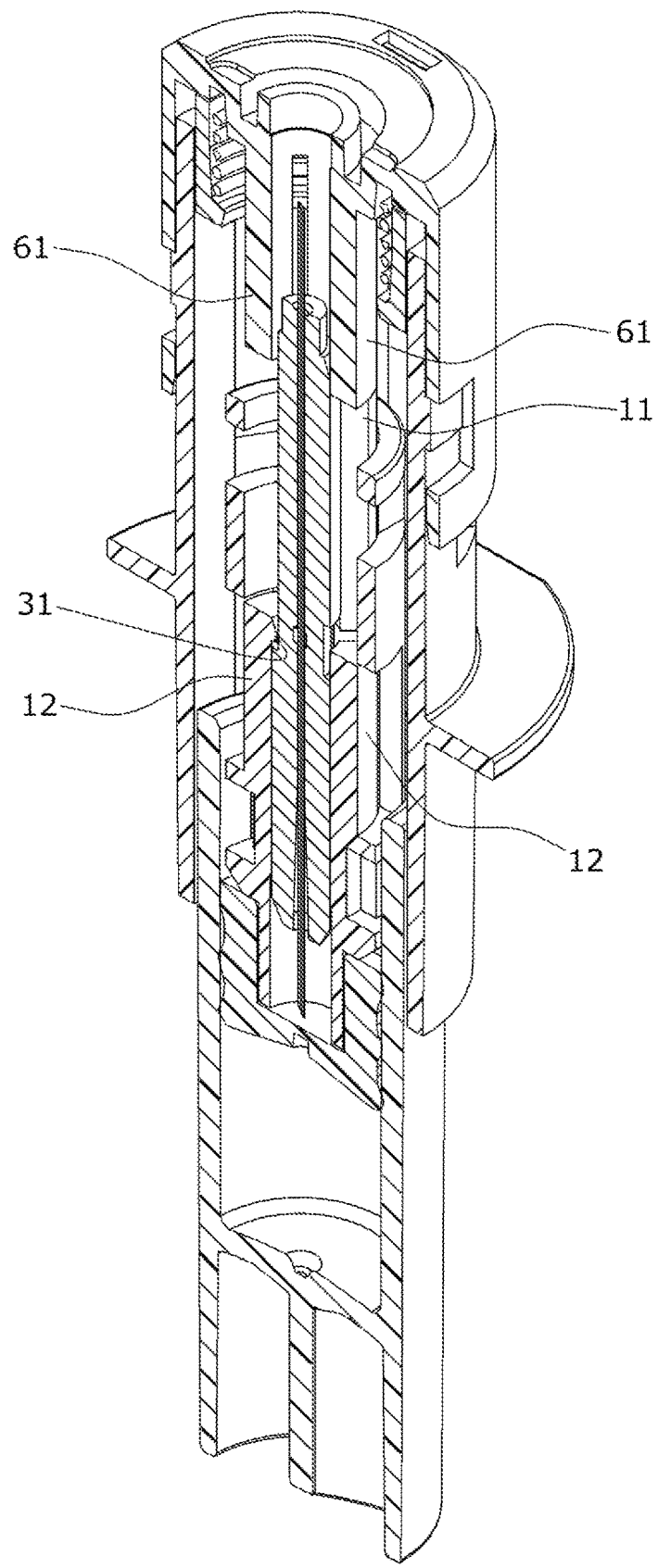
FIG. 11 is a perspective vertical cross section (X-Z cross section) of the syringe after a 90° rotation of the cover from the state shown in FIG. 1.
Figure 12:
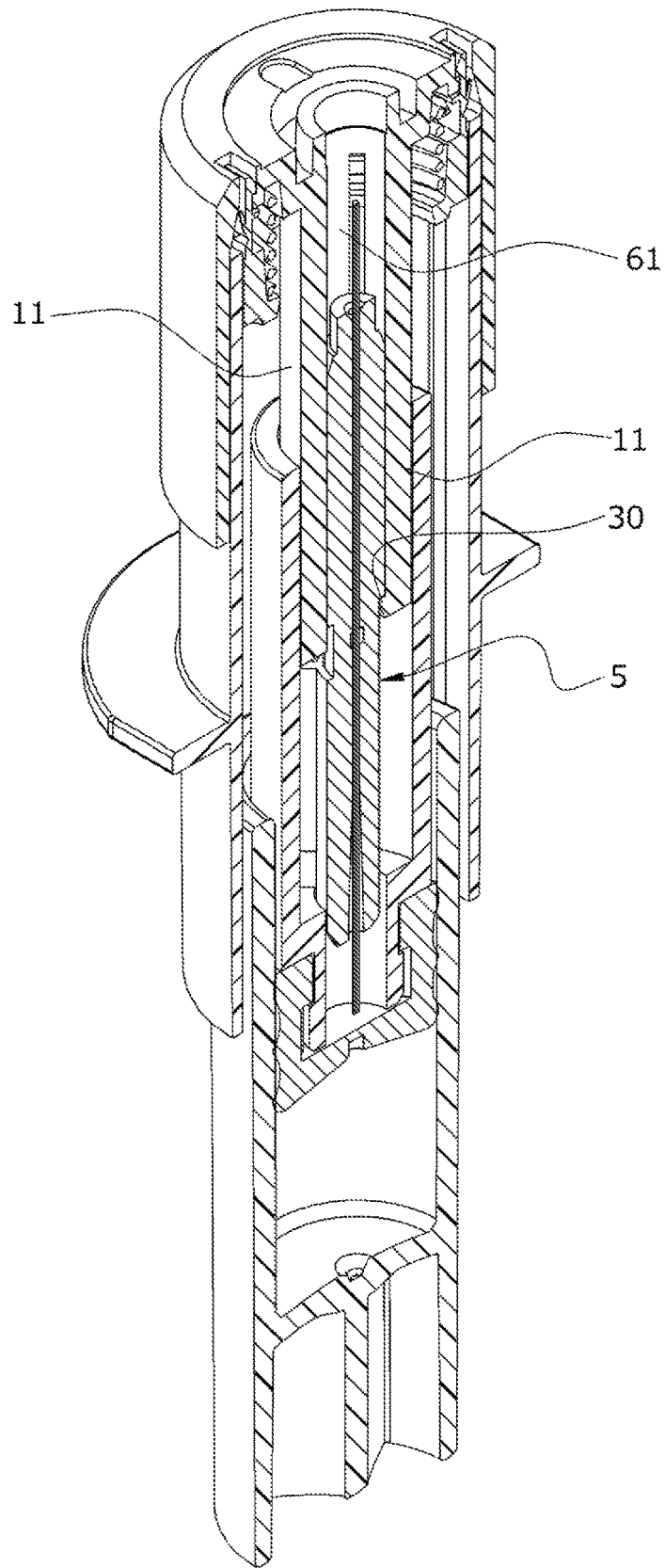
FIG. 12 is another perspective vertical cross section (Y-Z cross section) of the syringe in the state shown in FIG. 11.
Figure 13:
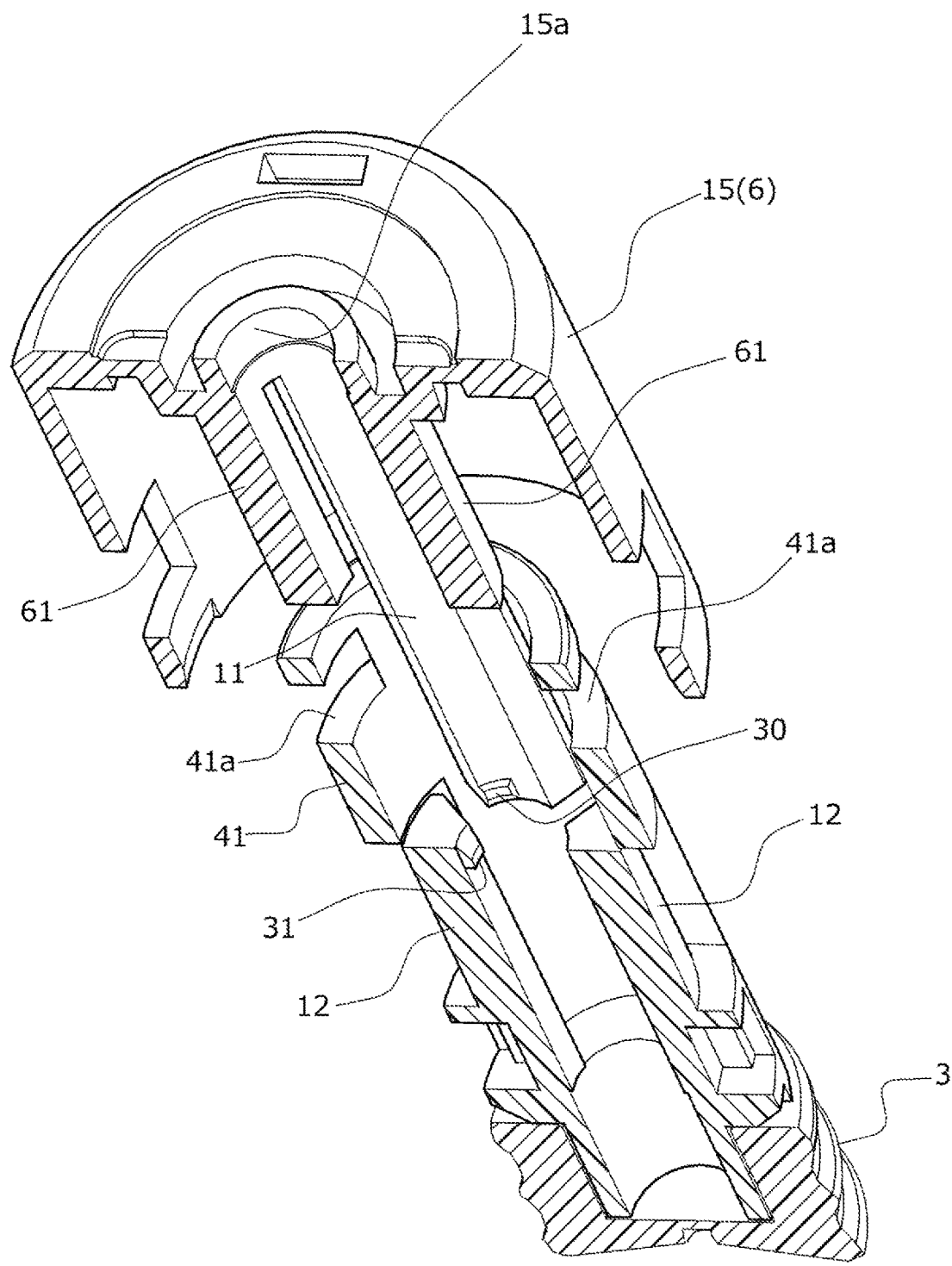
FIG. 13 is a perspective view of the syringe showing the relationship between the first cover member and plunger in the state shown in FIG. 11.
Figure 15:
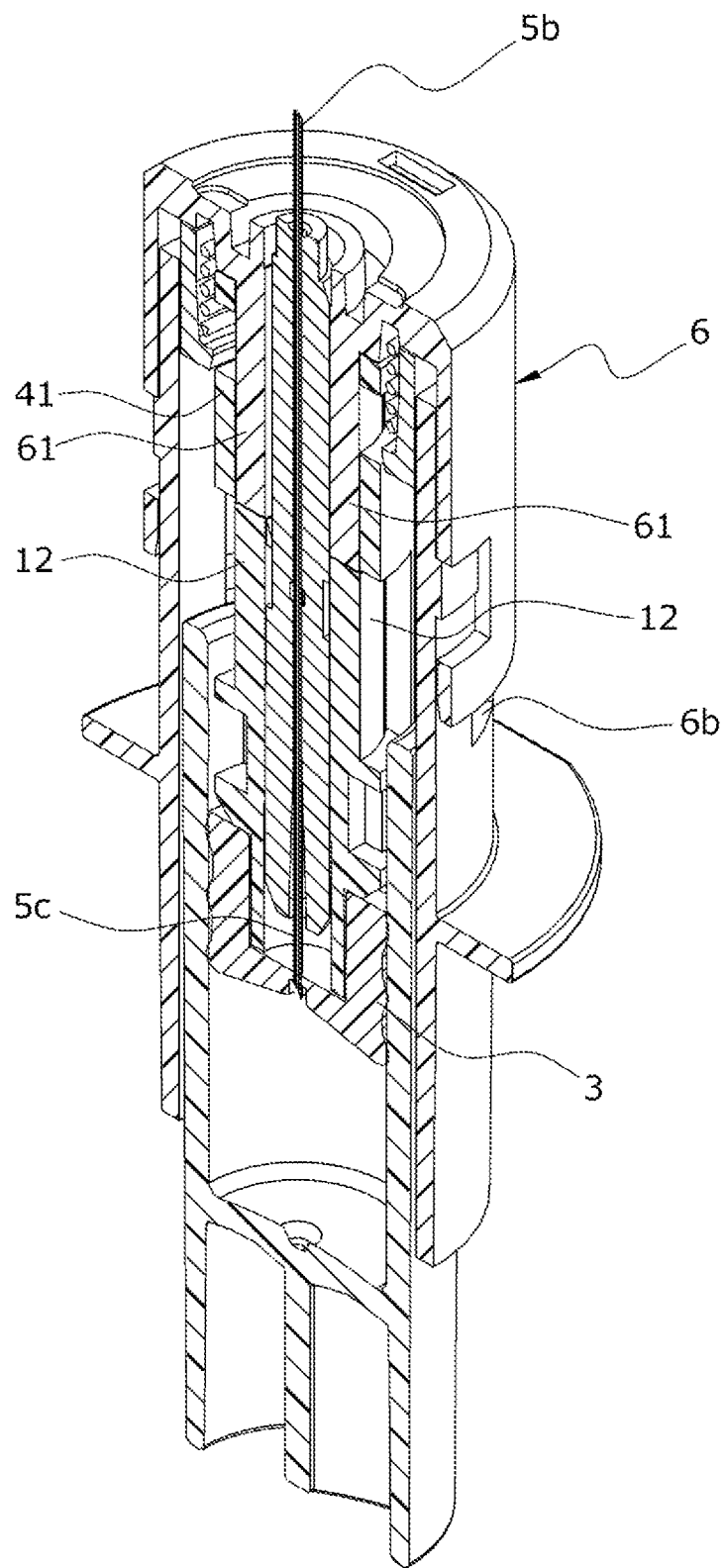
FIG. 15 is a perspective vertical cross section (X-Z cross section) of the syringe after the syringe barrel has been thrusted into the cover from the state shown in FIG. 11.
Figure 16:
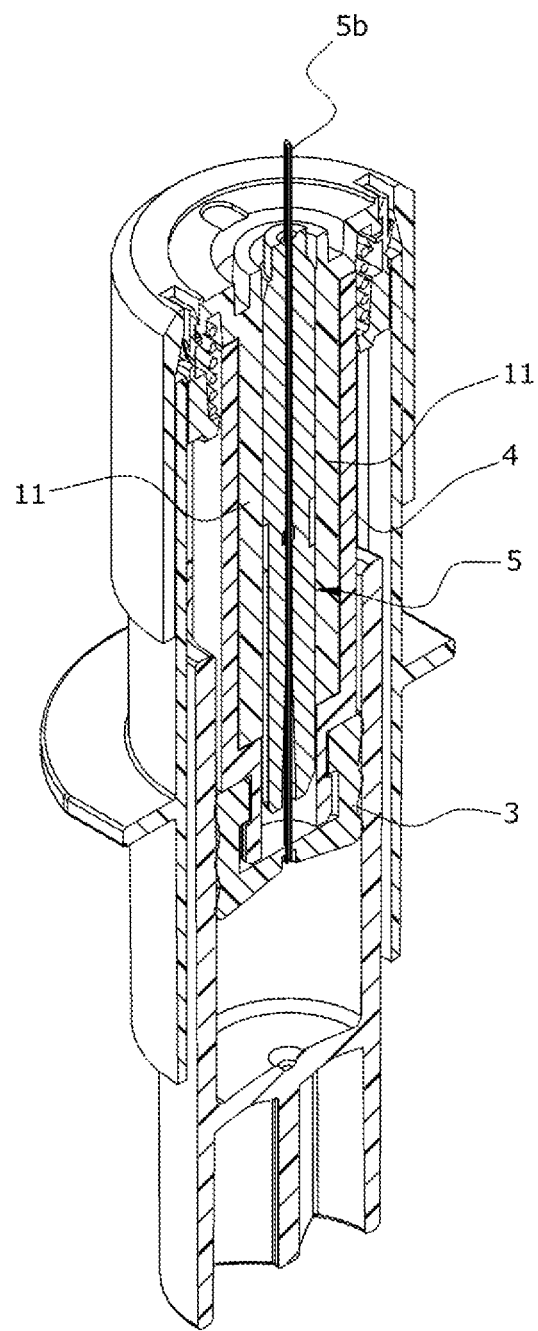
FIG. 16 is another perspective vertical cross section (Y-Z cross section) of the syringe in the state shown in FIG. 15.

During storage of the syringe 1, these first and second elastic engagement members 11 and 12 are arranged in the axial direction, as shown in FIGS. 1 and 2, and the base-end surface of each of the first elastic engagement members 11 and the distal-end surface of the corresponding one of the second elastic engagement members 12 are placed against each other and are locked in the axial direction in an extended state where the total length of the first and second elastic engagement members 11 and 12 is larger than the total length of the injection needle 5, thereby preventing the plunger 4 from being thrusted into the cover 6 in the locked position toward the distal end. In this extended state, the distal-end needle portion 5b of the injection needle 5 is placed within the cover 6. On the other hand, when the cover 6 is rotated relative to the plunger 4 by 90°, the plurality of second elastic engagement members 12 face the plurality of spaces defined by the first elastic engagement members 11, as shown in FIGS. 11 to 13 such that the first and second elastic engagement members 11 and 12 are arranged alternately in the circumferential direction; by thrusting the plunger 4 into the cover 6 in this unlocked position toward the distal end, the plurality of first elastic engagement members 11 alternately engage the plurality of second elastic engagement members 12, thereby reducing the total length of the cover 6 and plunger 4. When the total axial length of the cover 6 and plunger 4 is thus reduced, as shown in FIGS. 15 and 16, the base-end needle portion 5c of the injection needle 5 pierces through the gasket 3 and the distal-end needle portion 5b protrudes toward the distal end from the needle retraction hole 15a of the cover 6.

The first elastic engagement members 11 are integral with the cover plate on the distal-end portion of the cover 6 and extends from the back side of the cover plate toward the base end (i.e. downward in the drawings), and the elastic engagement members 11 are elastically deformable such that their base-end portions (i.e. bottom ends) are expanded in diameter. On the other hand, as shown in FIGS. 6 and 7, the second elastic engagement members 12 extend from an intermediate portion of the plunger 4 as determined along the axial direction toward the distal end (i.e. upward), and elastically deformable such that their distal-end portions (i.e. top ends) are expanded in diameter. The first elastic engagement members 11 have a larger axial length than the second elastic engagement members 12.

As shown in FIGS. 4 and 5, the needle base 5a of the injection needle 5 includes a first shaft portion 23 adjacent to the distal end around which the first elastic engagement members 11 are fitted during storage, a second shaft portion 24 adjacent to the base end around which the second elastic engagement members 12 are fitted, and a small-diameter shaft portion 25 provided between the first and second shaft portions 23 and 24.

Figure 9:
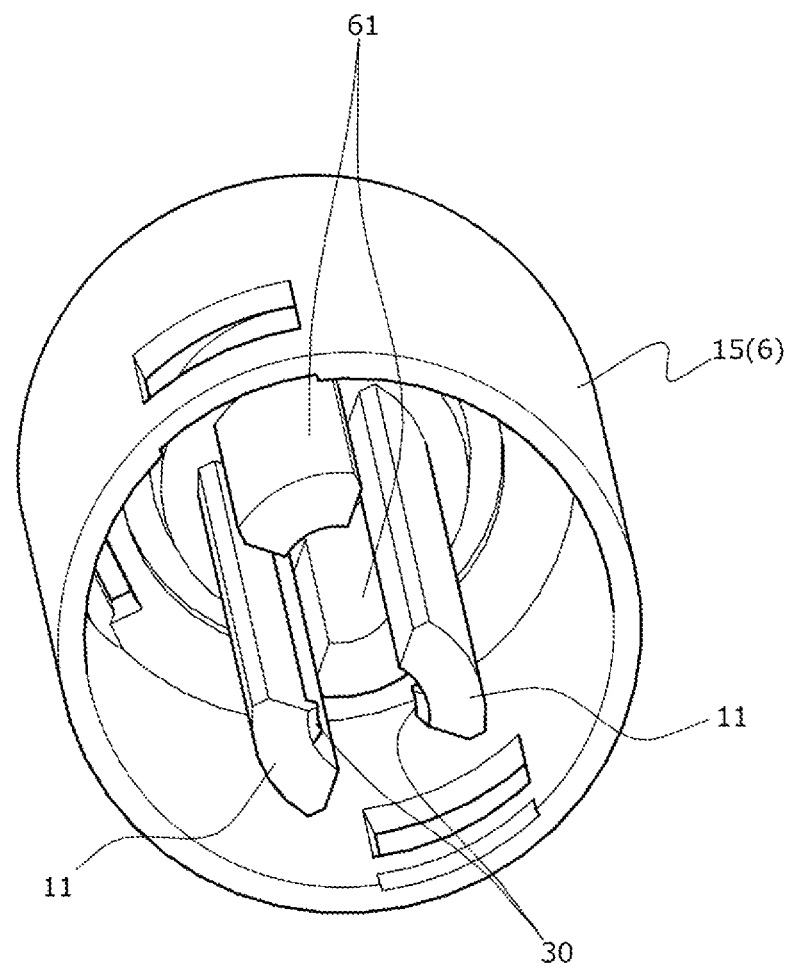
FIG. 9 is a perspective view of the first cover member, which constitutes the distal-end portion of the cover.

On the outer periphery of the first shaft portion 23 are provided, in places opposed in a diametrical direction: a pair of restriction ribs 26 for abutting the edges, as determined along the circumferential direction, of the first elastic engagement members 11 so as to allow the first elastic engagement members 11 to rotate up to about 90 degrees relative to the first shaft portion 23 but prevent them from relatively rotating more than about 90 degrees; and a pair of grooves 27 extending across the entire axial length of the first shaft portion 23. Further, on the outer periphery of the second shaft portion 24 are provided, in places opposed in a diametrical direction: four restriction ribs 28 at different circumferential positions for abutting the edges, as determined along the circumferential direction, of the second elastic engagement members 12 so as to prevent the second elastic engagement members 12 from rotating relative to the second shaft portion 24; and a pair of grooves 29 extending across the entire axial length of the second shaft portion 24. These two pairs of grooves 27 and 29 are located to be shifted in the circumferential direction. As shown in FIG. 9, a key 30 constituted by a protrusion is provided on the inner surface of the base-end portion of each of the first elastic engagement members 11, and, as shown in FIGS. 7 and 8, a key 31 constituted by a recess is provided on the inner surface of the distal-end portion of each of the second elastic engagement members 12.

In an initial state during storage, the keys 30 and 31 are located around the small-diameter shaft portion 25, where the keys 30 on the first elastic engagement members 11 engage, in the axial direction, the step between the small-diameter shaft portion 25 and first shaft portion 23, while the keys 31 on the second elastic engagement members 12 engage, in the axial direction, the step between the small-diameter shaft portion 25 and second shaft portion 24, thereby preventing the injection needle 5 from moving in the axial direction relative to the first and second elastic engagement members 11 and 12. During storage, the keys 31 on the second elastic engagement members 12 already face the grooves 27 on the first shaft portion 23 in the axial direction and, when the first elastic engagement members 11 are rotated about 90 degrees, the second elastic engagement members 12 are movable relative to the injection needle 5 toward the distal end, where the keys 31 move within the grooves 27 in the axial direction. On the other hand, during storage, the keys 30 on the first elastic engagement members 11 are located about 90 degrees relative to the grooves 29 on the second shaft portion 24. When the first elastic engagement members 11 are rotated about 90 degrees relative to the injection needle 5, the keys 30 face the grooves 29 in the axial direction such that the injection needle 5 is movable relative to the first elastic engagement members 11 toward the distal end, where the keys 30 move within the grooves 29 in the axial direction.

Further, when, beginning with the initial state, the cover 6 is rotated 90 degrees relative to the injection needle 2 and thrusted in, the first elastic engagement members 11 are thrusted relative to the injection needle 5 in the axial direction such that the distal-end needle portion 5b of the injection needle 5 protrudes from the needle retraction hole 15a of the cover 6, as shown in FIG. 15; at this time, the distal-end portions of the restriction ribs 28 on the first shaft portions 23 abut the top plate of the cover 6 in the axial direction to be located around the needle retraction hole 15a, thereby making it possible to force the injection needle 5 to be thrusted to the gasket 3 toward the base end.

To prevent the cover 6 from being rotated inadvertently relative to the plunger 4 from the initial state during storage, a protrusion 25a is provided on the outer periphery of the small-diameter shaft portion 25 of the needle base 5a of the injection needle 5, as shown in FIG. 5. When the cover 6 rotates from the locked position to the unlocked position, each first elastic engagement member 11 is slightly diametrically expanded/deformed and the keys 30 climb over the protrusion 25a. The resistance to the rotation operation at this moment prevents the cover 6 to be inadvertently rotated.

Further, according to the present embodiment, a cylindrical deformation-prevention part 41 is formed integrally with the plunger 4. This deformation-prevention part 41 is located closer to the distal end than the second elastic engagement members 12 are, and are fitted around the plurality of first elastic engagement members 11 in the initial state during storage to prevent the first elastic engagement members 11 from being diametrically expanded/deformed, thereby preventing the keys 30 on the first elastic engagement members 11 from being disengaged from the relevant step on the injection needle 5. Since the deformation-prevention part 41 is cylindrical in shape, the deformation prevention part 41 constantly prevents the first elastic engagement members 11 from being diametrically expanded/deformed even when the pair of first elastic engagement members 11 rotate relative to the deformation-prevention part 41. The inner diameter of the deformation-prevention part 41 is slightly larger than the outer diameter of the pair of first elastic engagement members 11 to permit the first elastic engagement members 11 to be slightly diametrically expanded/deformed to climb over the protrusion 25a.

When the plunger 4 is thrusted toward the distal end relative to the cover 6, as shown in FIGS. 15 and 16, the distal-end portion of the deformation-prevention part 41 is pushed against the cover plate of the cover 6 such that the second elastic engagement members 12 are separated from the cover plate by the axial length of the deformation-prevention part 41. According to the present embodiment, a pair of holding members 61 having an axial length substantially equal to that of the deformation-prevention part 41 extend, between the pair of first elastic engagement members 11, from the cover plate toward the base end as determined along the axial direction. Each of these holding members 61 has a transverse cross section that is substantially the same as that of the first elastic engagement members 11, and the holding members 61 and first elastic engagement members 11 are arranged alternately to be slightly separated in the circumferential direction. The above-discussed spaces for the engagement of the second elastic engagement members 12 are provided adjacent to the base-end portions of the holding members 61 (i.e. toward the bottom in the drawings).

When the first and second elastic engagement members 11 and 12 are extended, the holding members 61 are fitted around the outer periphery of the distal-end portion of the needle base 5a, as shown in FIG. 2, but are located closer to the distal end than the distal-end portions of the restriction ribs 26, thereby allowing the cover 6 to be rotated relative to the injection needle 5. At this moment, the injection needle 5 is supported by the cover 6 on four points i.e. on the two first elastic engagement members 11 and two holding members 61, thereby stabilizing the injection needle 5 in its held position. On the other hand, when the cover 6 is rotated from the initial state during storage by 90 degrees and then the plunger 4 is thrusted into the cover 6, the injection needle 5 moves in the axial direction relative to the cover 6 toward the distal end, and the restriction ribs 26 slide in the axial direction within the slits between the holding members 61 and first elastic engagement members 11. At this time, in addition to the support on four points, the engagement of the restriction ribs 26 and the slits stabilizes the injection needle 5 in its held position to enable causing the injection needle 5 to protrude more smoothly.

Figure 3:
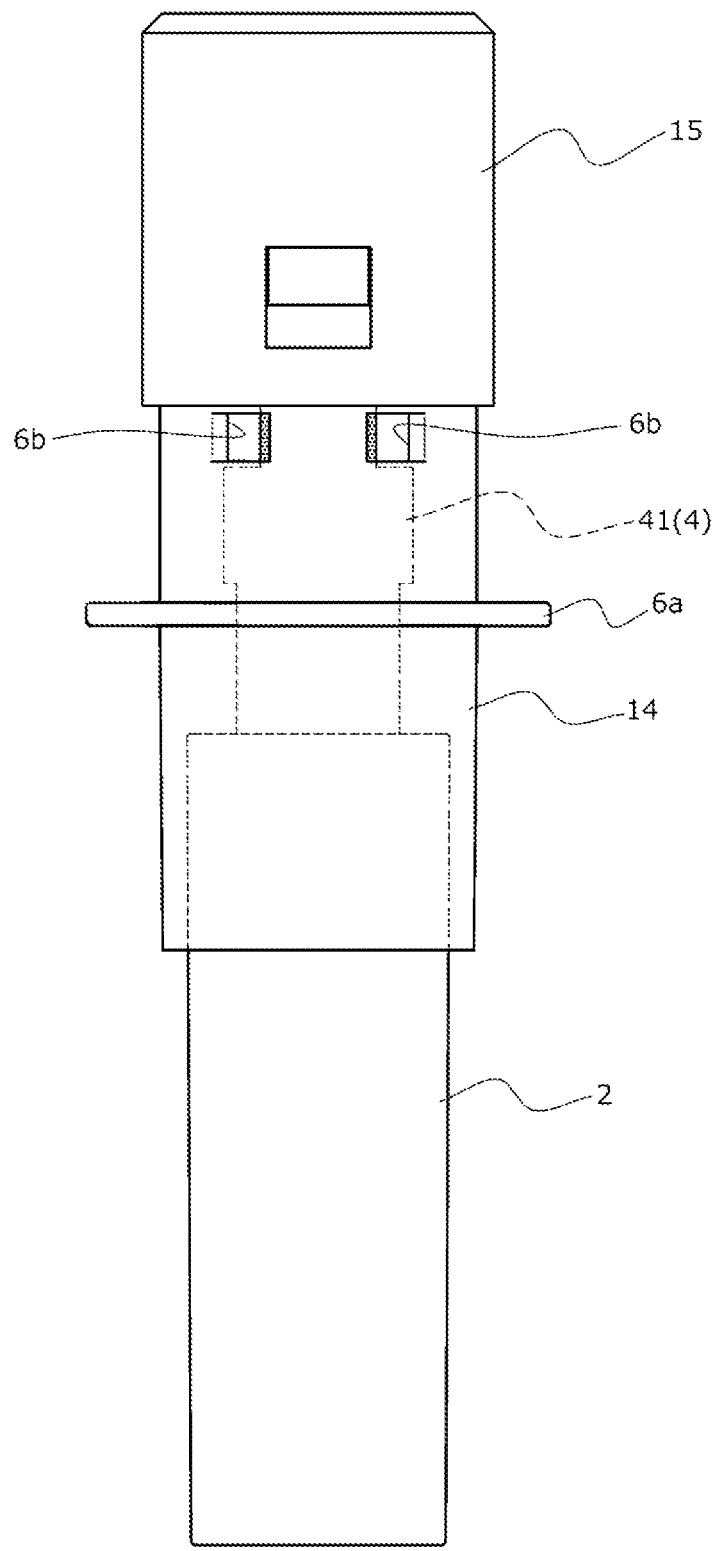
FIG. 3 is a front view of the syringe in the state shown in FIG. 1.

Further, the outer periphery of the deformation-prevention part 41 is covered with the first cover member 14 of the cover 6. A pair of recesses 41a are provided in a pair of opposite portions of the deformation-prevention part 41 arranged in a diametrical direction and occupying a part of the deformation-prevention part as determined along the axial direction, each recess 41a extending through in a direction (Y-direction) perpendicular to the diametrical direction (X-direction). Preferably, each recess 41a may be formed by flat surfaces extending in this perpendicular direction along the edges, as determined along the circumferential direction, of the associated through-hole extending through the deformation-prevention part 41 in a radial direction. On the first cover member 14 are provided peepholes 6b that face a recess 41a in its direction of through-extension when in the locked position, as shown in FIG. 3, and face the deformation-prevention part 41 when in the unlocked position. A total of four peepholes 6b are provided, a peephole provided on each of the sides, as determined along the direction of through-extension, of each of the two recesses 41a.

Figure 14:
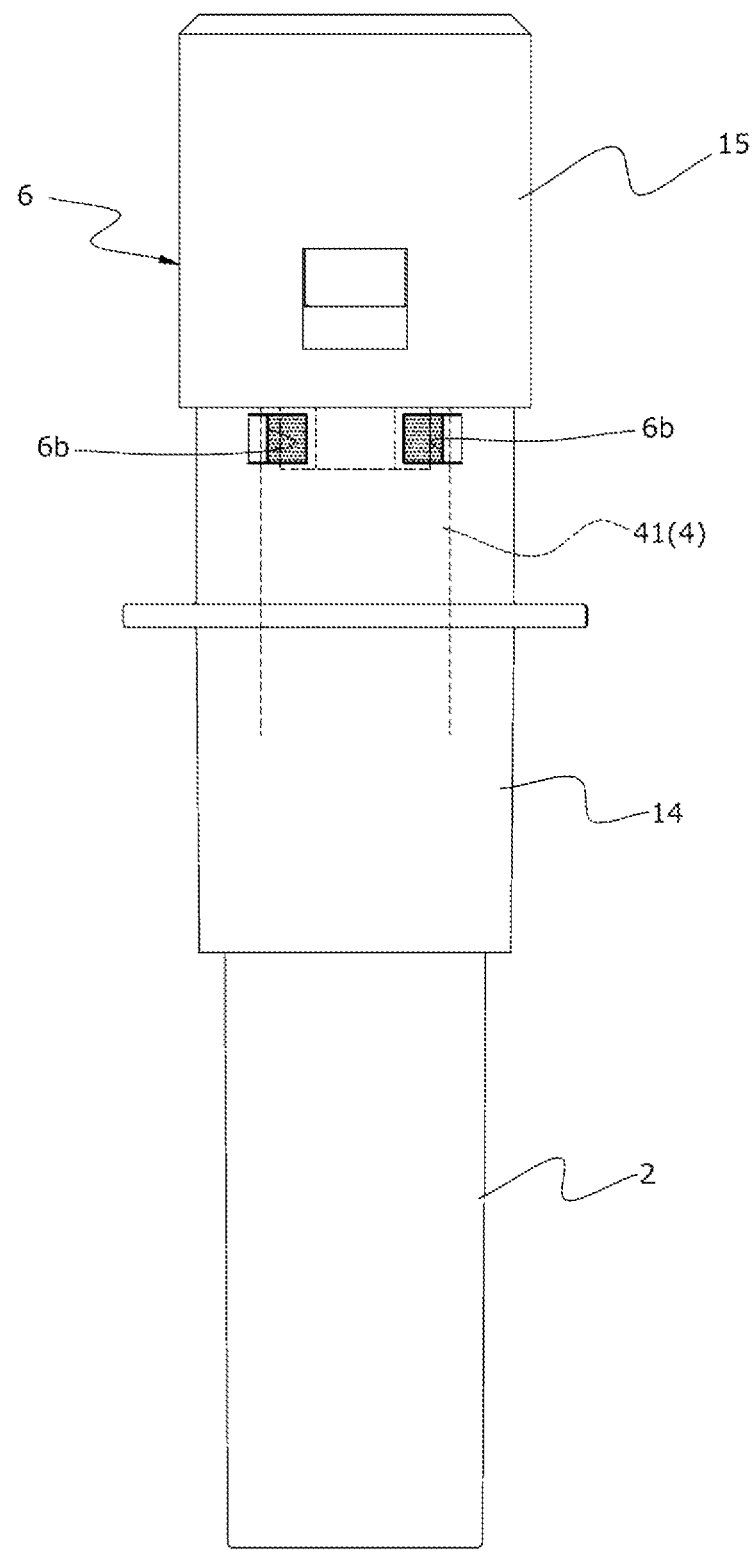
FIG. 14 is a front view of the syringe in the state shown in FIG. 11.

If the plunger 4 is in a color that is different from those of the other components and thus is conspicuous, e.g. red, when the cover 6 is in the locked position, the red portions (i.e. dotted portions in the drawings) are hardly visible in the peepholes 6b, as shown in FIG. 3, and, when the cover 6 is rotated to the unlocked position, the peepholes 6b are filled with red, as shown in FIG. 14. Thus, the deformation-prevention part 41 functions as an indicator that allows the current state of the cover 6 to be quickly determined by visual inspection.

The peepholes 6b of the present embodiment are constituted by the second engagement recesses (see Patent Document 1) to which the elastic engagement members of the ring of the spring holder 17 engage when, after administration, the ring has been moved by the spring 16 toward the base end relative to the cover 6.

To assemble the syringe 1, first, the spring 16 and spring holder 17 are combined with the cover 6 and the pair of first elastic engagement members 11 of the cover 6 are diametrically expanded/deformed and the injection needle 5 is mounted inside, and the keys 30 on the first elastic engagement members 11 are engaged with the small-diameter shaft portion 25 of the injection needle 5 before the plunger 4 is strongly thrusted to the first elastic engagement members 11 and injection needle 5 such that the keys 31 on the second elastic engagement members 12 also engage with the small-diameter shaft portion 25 of the injection needle 5.

The present invention is not limited to the above-described embodiment, and can be modified in design as appropriate. For example, the injection needle may be not rotatable around its axis relative to the first elastic engagement members but rotatable around its axis relative to the second elastic engagement members. Furthermore, three or more first elastic engagement members may be provided, and three or more second elastic engagement members may be provided.

Figure 17:
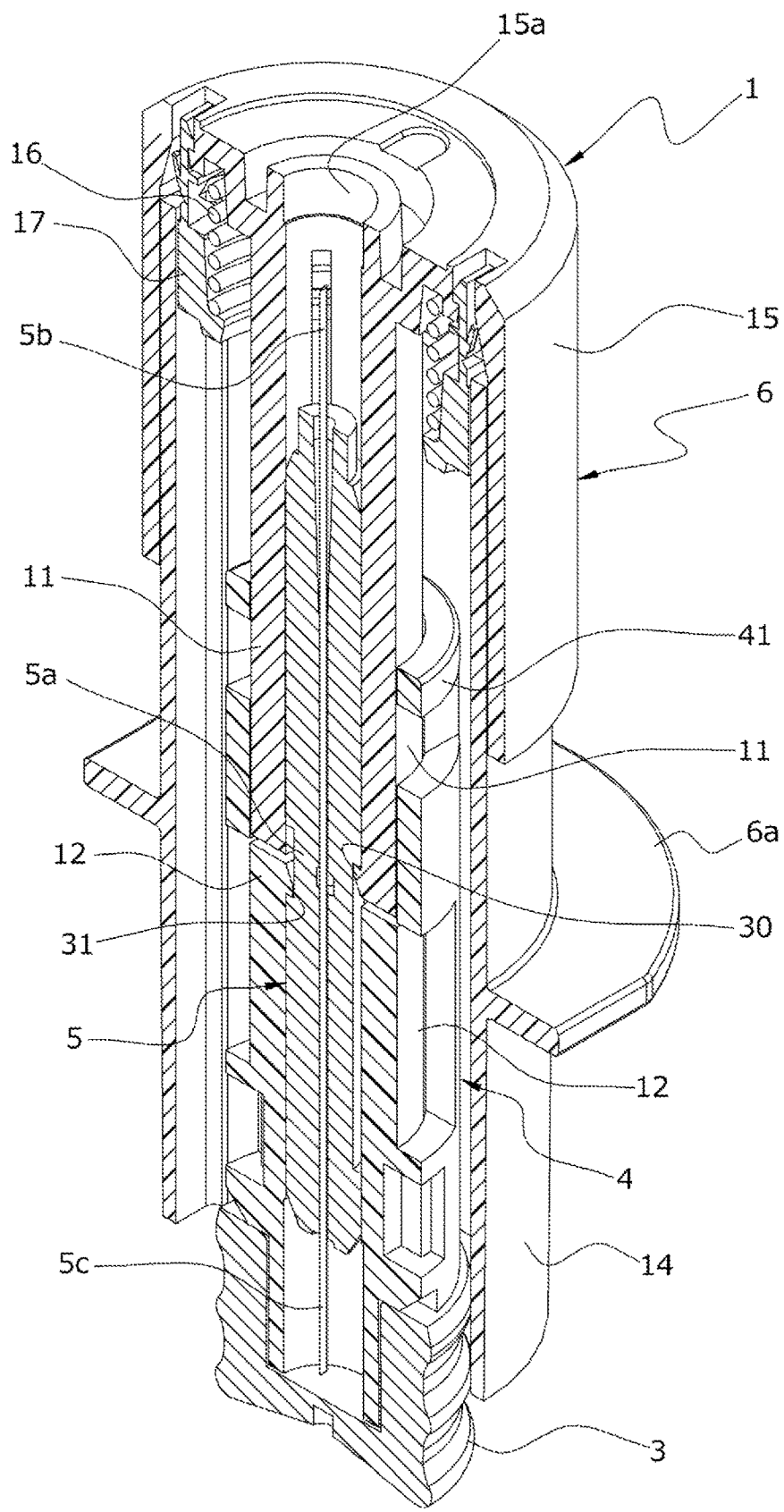
FIG. 17 is a perspective vertical cross section of a syringe according to another embodiment of the present invention during storage.
Figure 18:
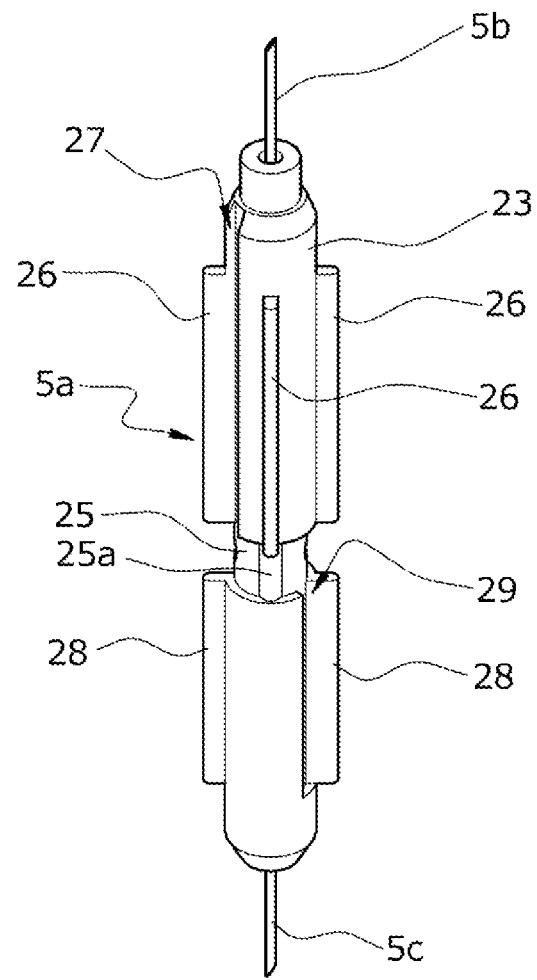
FIG. 18 is a perspective view of the entire injection needle of the syringe of FIG. 17.

FIGS. 17 and 18 illustrate another embodiment of the present invention that represents an improvement over the syringe of the above-described embodiment. The same components as in the above-described embodiment are labeled with the same reference characters and their detailed description will not be given, and the components and effects that are different will be described. In FIG. 17, the syringe barrel is not shown.

In this improved embodiment, the injection needle 5 is mounted in the top-bottom direction opposite to that in the above-described embodiment, as shown in FIG. 18, and the injection needle 5 is prevented from rotating relative to the cover 6 and is allowed to rotate relative to the plunger 4 up to about 90 degrees. That is, in order to prevent the first elastic engagement members 11 from rotating relative to the first shaft portion 23 of the injection needle 5, four restriction ribs 26 are provided at different circumferential locations on the outer periphery of the first shaft portion 23 to abut the edges, as determined along the circumferential direction, of the first elastic engagement members 11, and a pair of grooves 27 extending across the entire axial length of the first shaft portion 23 so as to be arranged in places opposed in a diametrical direction. On the other hand, on the outer periphery of the second shaft portion 24 are provided, arranged in places opposed in a diametrical direction: a pair of restriction ribs 28 for abutting the edges, as determined along the circumferential direction, of the second elastic engagement members 12 in order to allow the second elastic engagement members 12 from rotating relative to the second shaft portion 24 up to about 90 degrees but prevent them from relatively rotating more than about 90 degree; and a pair of grooves 29 extending from the small-diameter shaft portion 25 toward the base end. The grooves 29 of the present embodiment extend midway through the axial length of the second shaft portion 24. The rotation operation of the plunger 4 can be indirectly made by rotating the syringe barrel 2. That is, when the syringe barrel 2 is rotated, the gasket 3 fitted in the syringe barrel 2 is rotated by means of friction resistance. As the plunger 4 engages the gasket 3 so as to be not rotatable, the plunger 4 can be rotated relative to the cover 6 and injection needle 5.

During storage, the keys 30 on the first elastic engagement members 11 already face the grooves 29 of the second shaft portion 24 in the axial direction, and rotating the second elastic engagement members 12 by about 90 degrees makes the injection needle 5 movable relative to the first elastic engagement members 11 toward the distal end, where the keys 30 move in the axial direction within the grooves 29. On the other hand, during storage, the keys 31 on the second elastic engagement members 12 are positioned about 90 degrees relative to the grooves 27 on the first shaft portion 23. When the second elastic engagement members 12 is rotated relative to the injection needle 5 by about 90 degrees, the keys 31 face the grooves 27 in the axial direction, at which time the second elastic engagement members 12 are movable relative to the injection needle 5 toward the distal end, where the keys 31 move in the axial direction within the grooves 27.

Further, according to this improved embodiment, the plunger 4 is rotated relative to the injection needle 5 and, during this rotation, the second elastic engagement members 12 are slightly diametrically expanded/deformed and the keys 31 climb over the protrusion 25a. Thus, the first elastic engagement members 11 are constructed not to be deformed at all during administration, and thus the size of the gap between the first elastic engagement members 11 and deformation-prevention part 41 can be minimized. On the other hand, the axial length of the second elastic engagement members 12 may be smaller than the axial length of the first elastic engagement members 11, thereby providing sufficient toughness of the second elastic engagement members 12.

The invention claimed is:

1. A syringe comprising:
    a syringe barrel having an open distal-end portion and having an interior space to be filled with a liquid drug;
    a gasket fitted into the syringe barrel to seal in the liquid drug; an injection needle having a base-end portion adapted to pierce through the gasket at least during administration of the liquid drug;
    a plunger attached to the gasket and holding the injection needle; and
    a cover provided adjacent to a distal-end portion of the plunger,
    wherein the cover includes a plurality of first elastic engagement members for holding the injection needle, the first elastic engagement members being spaced apart from each other in a circumferential direction and capable of being deformed so as to be diametrically expanded,
    the cover is capable of moving in an axial direction relative to the injection needle between a state where a distal-end portion of the injection needle is housed within the cover and a state where the distal-end portion of the injection needle protrudes from a distal-end portion of the cover, and
    the elastic engagement members of the cover in the housing state and the injection needle engage so as to prevent the injection needle from being withdrawn from the elastic engagement members of the cover, and this engagement is released as the elastic engagement members are diametrically expansively deformed,
    characterized in that the plunger includes an integrated deformation-prevention part covering outer peripheries of the plurality of elastic engagement members so as to prevent the engagement from being released by the elastic engagement members being diametrically expansively deformed,
    wherein
        the plunger includes a plurality elastic engagement members for holding the infection needle, the plurality of second elastic engagement members being separated from each other in the circumferential direction and being capable of being diametrically expanded/deformed, and
        the deformation-prevention part is located closer to a distal end than the second elastic engagement members.

2. The syringe according to claim 1, wherein the cover is rotatable relative to the plunger between a locked position where the plurality of second elastic engagement members of the plunger are aligned with the plurality of first elastic engagement members to be arranged in an axial direction and an unlocked position where the plurality of second elastic engagement members face a plurality of spaces defined by the first elastic engagement members,
    by thrusting the plunger into the cover in the unlocked position toward the distal end, the plurality of first elastic engagement members alternately fit to the plurality of second elastic engagement members to reduce a total length of the cover and plunger, and
    the deformation-prevention part covers the outer peripheries of the plurality of first elastic engagement members in both the locked position and the unlocked position.

3. The syringe according to claim 2, wherein the cover includes: a cylindrical portion, the syringe barrel being inserted into the cylindrical portion to be movable in the axial direction; a cover plate closing a distal-end opening of the cylindrical portion; the plurality of first elastic engagement members extending from the cover plate toward the base end as determined along the axial direction; and a plurality of holding members located between the plurality of first elastic engagement members and extending from the cover plate toward the base end as determined along the axial direction, the holding members and the first elastic engagement members being separated from each other in the circumferential direction, and the first elastic engagement members being elastically deformable such that their base-end ends move radially outward,
    the first elastic engagement members extend farther toward the base end than the holding members, thereby providing the spaces adjacent to base-end ends of the holding members, and
    the plurality of holding members work together with the plurality of first elastic engagement members to hold the injection needle.

4. The syringe according to claim 3, wherein the deformation-prevention part is cylindrical in shape.

5. The syringe according to claim 4, wherein an outer periphery of the deformation-prevention part of the plunger is covered with the cover, and a pair of recesses are provided in a pair of opposite portions of the deformation-prevention part of the plunger arranged in a diametrical direction and occupying a part of the deformation-prevention part as determined along the axial direction, each recess extending through in a direction perpendicular to the diametrical direction, and a peephole is provided in the cover, the peephole facing one of the recesses such that they are arranged in a direction of through-extension when the cover is at one of the locked position and the unlocked position, and facing the deformation-prevention part when the cover is at another position.

* * * * *